(12) United States Patent
Van Wiemeersch

(10) Patent No.: US 10,433,984 B2
(45) Date of Patent: Oct. 8, 2019

(54) ADD-ON CAPACITIVE TOUCHSCREEN AID

(71) Applicant: FORD GLOBAL TECHNOLOGIES, LLC, Dearborn, MI (US)

(72) Inventor: John Robert Van Wiemeersch, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 868 days.

(21) Appl. No.: 14/260,956

(22) Filed: Apr. 24, 2014

(65) Prior Publication Data

US 2014/0236314 A1   Aug. 21, 2014

Related U.S. Application Data

(62) Division of application No. 13/443,104, filed on Apr. 10, 2012, now abandoned.

(51) Int. Cl.
| | |
|---|---|
| *A61F 2/54* | (2006.01) |
| *A61F 2/58* | (2006.01) |
| *A61F 4/00* | (2006.01) |
| *G06F 3/044* | (2006.01) |
| *A61F 2/50* | (2006.01) |

(52) U.S. Cl.
CPC ............... *A61F 2/583* (2013.01); *A61F 2/54* (2013.01); *A61F 4/00* (2013.01); *G06F 3/044* (2013.01); *A61F 2/586* (2013.01); *A61F 2/588* (2013.01); *A61F 2002/5001* (2013.01); *A61F 2002/5061* (2013.01); *A61F 2002/543* (2013.01)

(58) Field of Classification Search
CPC ...... A61F 2/586; A61F 2/54; A61F 2002/5061
See application file for complete search history.

(56) References Cited

U.S. PATENT DOCUMENTS

| | | | | |
|---|---|---|---|---|
| 2008/0015426 A1* | 1/2008 | Sanfilippo | ............ | A61B 5/0416 600/391 |
| 2011/0278061 A1* | 11/2011 | Farnan | ............... | A41D 19/0024 174/70 R |
| 2013/0076699 A1* | 3/2013 | Spencer | .................. | G06F 3/044 345/179 |

* cited by examiner

*Primary Examiner* — Bruce E Snow
(74) *Attorney, Agent, or Firm* — LeClairRyan

(57) ABSTRACT

An apparatus that allows a glove wearer or the wearer of a prosthetic limb to operate a device having a capacitive touchscreen is disclosed. There are three solutions provided in the disclosed invention. The first embodiment of the disclosed invention is directed to a conductive finger sock that can be applied to a digit of a non-conductive artificial limb. The finger sock may cover the whole digit of the artificial limb or may cover only the tip. The second embodiment is an adhesive element having a conductive material such as a conductive thread or a conductive sponge material. The adhesive element can be attached to a glove or to a prosthetic limb or may be used as an actual bandage. The third embodiment of the disclosed invention is directed to a factory integrated conductive tip that is part of a digit of a non-conductive artificial limb. Regardless of the embodiment, the conductive element may be attached to the wearer's skin by a conductive line or may be used without the conductive line and thus may function in isolation.

6 Claims, 5 Drawing Sheets

ADD-ON CAPACITIVE TOUCHSCREEN AID

CROSS-REFERENCE TO RELATED APPLICATIONS

This application is a divisional application of U.S. patent application Ser. No. 13/443,104 (filed Apr. 10, 2012), which is incorporated herein in its entirety.

TECHNICAL FIELD

The disclosed invention relates generally to capacitive touchscreens and to the operation of capacitive touchscreens. More particularly, the disclosed invention relates to an aid that may be attached to a prosthetic limb as a sock, may be attached to a variety of surfaces as an adhesive aid or may be integrated with a prosthetic limb. The disclosed invention allows the wearer to operate a capacitive touchscreen without limitations ordinarily associated with such use.

BACKGROUND OF THE INVENTION

The capacitive touchscreen relies on the capacitance of the human body to break or alter an electric field set up around a button so configured. Capacitive sensing is a general phrase that includes a variety of different methods of achieving capacitive coupling. Many sensors rely on capacitive technology, such as position sensors, moisture level sensors, fluid level sensors and the like. Capacitive sensors do not rely on mechanical elements, thus increasing reliability. Because of their relatively low production cost and high degree of durability, capacitive sensors find multiple applications in a broad variety of areas.

In the computer area, capacitive sensing often finds applications as a human interface device. The capacitive sensing device used most often in this application is the capacitive touchscreen which is used in hand-held communication devices of all kinds, such as mobile phones, and other mobile information devices.

The typical capacitive touchscreen includes an insulator screen. The insulator typically is glass. A coating of a transparent conductor, such as indium tin oxide (ITO), is formed over the insulator glass. In operation, the screen sets up an electrostatic field. When the human finger, having a charge of its own, comes into contact with the touchscreen a distortion of the screen's electrostatic field results. This distortion is measurable as a change in capacitance.

While this arrangement is suitable for many applications it is not applicable in those applications where no direct contact between the capacitive touchscreen and the human operator can be made. This situation can arise in many situations, including where the user wears thick gloves or where the user has a prosthetic limb. In both cases the charge of the human finger or electrical some form of conductivity is not present and the field on the screen is thus not distorted.

Accordingly, as in so many areas of vehicle technology, there is room in the art of capacitive touchscreens for an alternative configuration that allows glove wearers or wearers of prosthetic limbs to operate the touchscreen.

SUMMARY OF THE INVENTION

The disclosed invention provides solutions to the challenges faced by both the wearers of gloves and the wearers of prosthetic devices when trying to operate devices having capacitive touchscreens. There are three solutions provided in the disclosed invention. Each of the solutions offers the user with a practical and effective approach to operating a capacitive touchscreen.

The first embodiment of the disclosed invention is directed to a conductive finger sock that can be applied to a digit of a non-conductive artificial limb. The finger sock may cover the whole digit of the artificial limb or may cover only the tip. The finger sock may be connected by lead wire to a patch on an area of the user's skin, thereby providing the tip of the finger sock with the electrical charge from the user's skin, or may be isolated.

The second embodiment is an adhesive element having a conductive material such as an conductive thread or a conductive sponge material. Like the first embodiment, a lead wire may be provided for attachment to the user's skin or may be isolated. The adhesive element may be applied to a variety of surfaces, including an artificial limb, a glove, or may be used as an actual bandage.

The third embodiment of the disclosed invention is directed to a factory integrated conductive tip that is part of a digit of a non-conductive artificial limb. The conductive tip may be connected by lead wire to a patch on an area of the user's skin, thereby providing the tip of the finger sock with the electrical charge from the user's skin, or may be isolated.

Other advantages and features of the invention will become apparent when viewed in light of the detailed description of the preferred embodiment when taken in conjunction with the attached drawings and the appended claims.

BRIEF DESCRIPTION OF THE DRAWINGS

For a more complete understanding of this invention, reference should now be made to the embodiments illustrated in greater detail in the accompanying drawings and described below by way of examples of the invention wherein.

DETAILED DESCRIPTION OF THE PREFERRED EMBODIMENT

Figure 1:
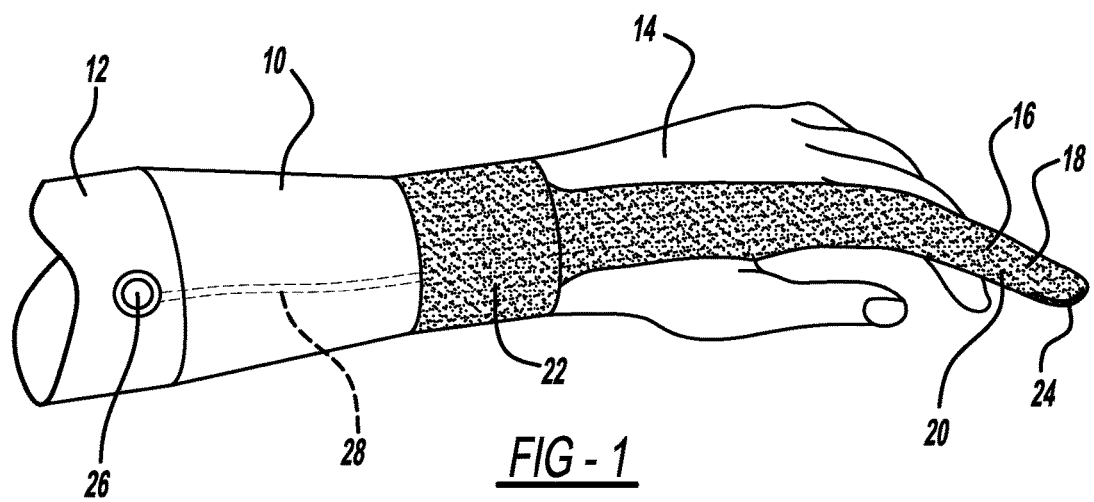
FIG. 1 is a side view of a prosthetic device having a conductive sock attachment of the disclosed invention substantially placed over one finger.

In the following figures, the same reference numerals will be used to refer to the same components. In the following description, various operating parameters and components are described for different constructed embodiments. These specific parameters and components are included as examples and are not meant to be limiting.

Figure 2:
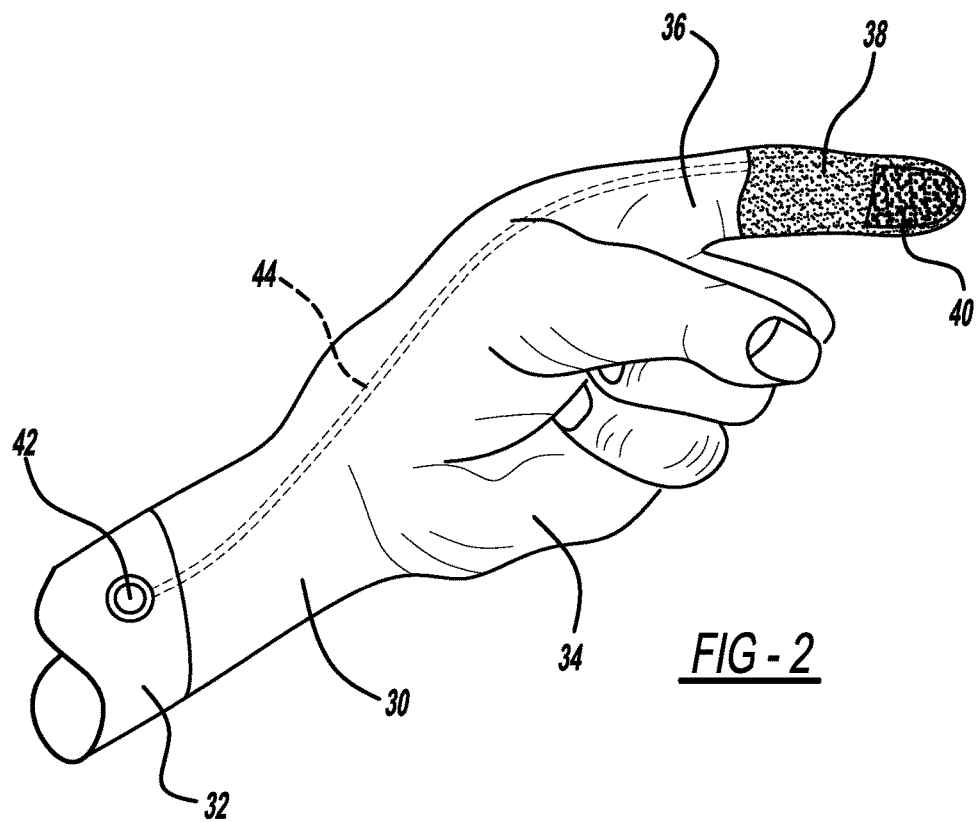
FIG. 2 is a side view of a prosthetic device having an alternative conductive sock attachment of the disclosed invention partially covering one finger.

FIGS. 1 and 2 relate to a conductive sock or tip that can be attached to a finger of a prosthetic device. The embodiment illustrated in FIG. 1 covers substantially all of the finger while the embodiment illustrated in FIG. 2 covers only a portion of the finger. Selecting between the two would be the choice of the wearer.

With respect to FIG. 1, a side view of a prosthetic device 10 is illustrated. The prosthetic device 10 is attached to the user's forearm 12. It is to be understood that the illustrated prosthetic device 10 as well as those shown in throughout the illustration and description of the disclosed invention are for discussion purposes only as variations of these configurations as well as other prosthetic devices may be used in conjunction with the adhesive patch of the disclosed invention.

The prosthetic device 10 includes a body portion 14 and a finger 16. Attached to the finger 16 is an aid of the disclosed invention in the form of a finger sock 18. The sock 18 may be composed of any one of several materials and may be woven or formed in any one of a variety of known methods. The finger sock 18 includes a finger portion 20 and a wrist portion 22.

Attached to the tip of the finger portion 20 of the finger sock 18 is a conductive portion 24. The conductive portion 24 may be formed from any of several electrically conductive media, such as a conductive thread, conductive wire or conductive foam.

In order to convey an electric current between the conductive portion 24 and the user's forearm 12 a conductive arrangement is provided. Particularly, a skin-contacting adhesive patch 26 is provided for attachment to the user's skin. The skin-contacting adhesive patch 26 includes an adhesive portion for attachment to the skin and a conductive portion that is placed into contact with the wearer's skin when the skin-contacting adhesive patch 26 is used. A conductive line 28 is almost entirely embedded in the prosthetic device 70 and connects the electrically conductive medium of the pad conductive portion 24 with the conductive portion of the skin-contacting adhesive patch 26.

The conductive sock 18 may be used with or without the conductive line 28 and the adhesive patch 26. The complete circuit presented by use of the conductive line 28 and the adhesive patch 26 is needed in applications where the connection back to the body portion 12 is needed. One such situation is in the automotive setting where a vehicle operator must use a vehicle center screen that can detect if the driver or passenger is attempting to push screen commands. If the vehicle is moving, they will not accept commands from the driver but will accept commands from the passenger. In such a circumstance the unit determines the source by looking at the capacitive circuit between the display surface, the hand and the body, and the top of the seat cushion. In such a situation a complete circuit would be needed.

Alternatively, while it may be helpful or necessary to have an electrical connection made by the conductive line 28 and the adhesive patch 26, such an arrangement is not necessary in all computer human machine interface (HMI) situations. For example, it is known to use a plastic stylus to operate a touch screen. Being of a plastic construction the stylus is not conductive, but instead includes a conductive foam tip that breaks the field of the capacitive sensor or switch. Such an arrangement is sufficient to effectively operate most applications such as iPads™ iPods™, or any of a variety of electronic communication tablets.

With respect to FIG. 2, a side view of a prosthetic device 30 is illustrated. The prosthetic device 30 is attached to the user's forearm 32. The prosthetic device 30 includes a body portion 34 and a finger 36. Attached to the finger 36 is a finger tip sock 38 which is an alternate embodiment of the finger sock 18 shown in FIG. 1 and discussed in relation thereto. As is the case for the sock 18, the finger tip sock 38 may be composed of any one of several materials and may be woven or formed in any one of a variety of known methods.

Attached to the tip of the finger tip sock 38 is a conductive portion 40. The conductive portion 40 may be formed from any of several electrically conductive media, such as a conductive thread, conductive wire or conductive foam. An optional adhesive patch 42 and optional conductive line 44 may be provided.

Figure 3:
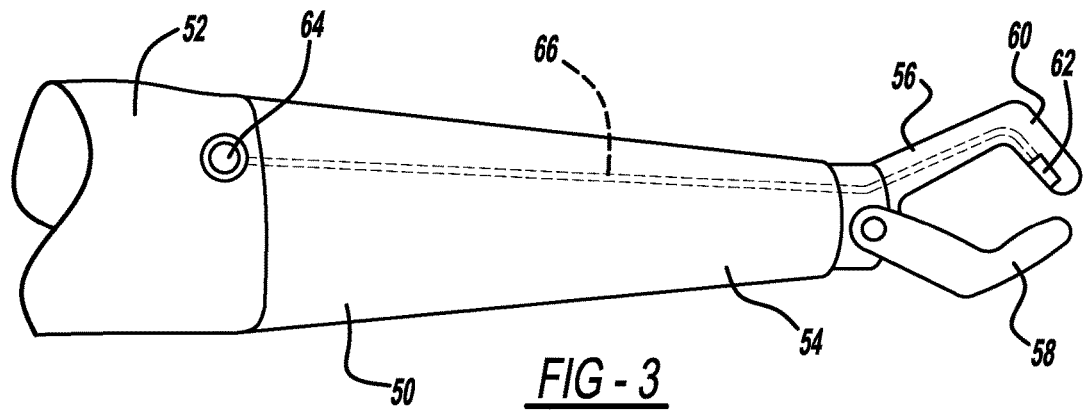
FIG. 3 is a side view of a prosthetic device having a conductive adhesive aid of the disclosed invention fitted thereto.
Figure 4:
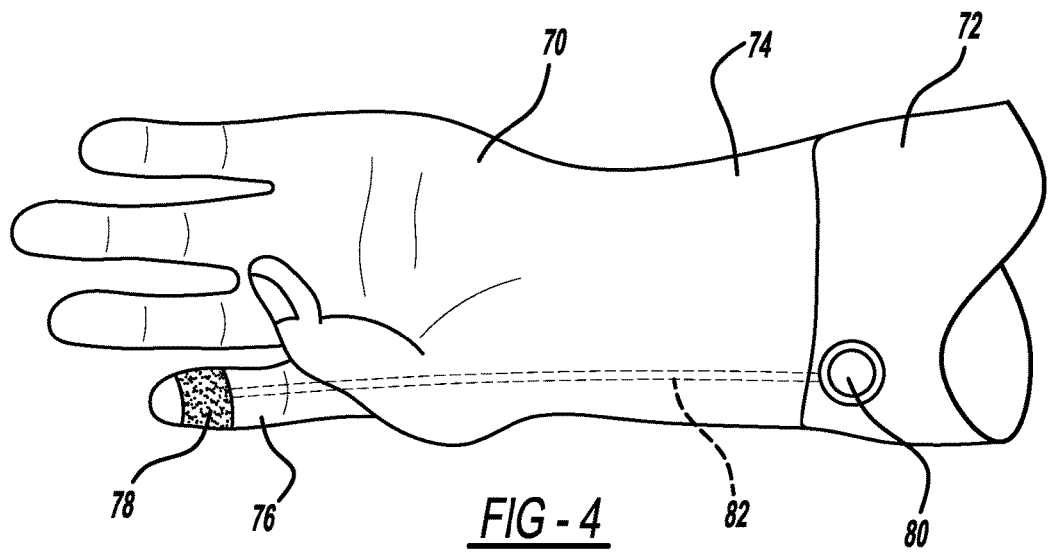
FIG. 4 is a side view of a prosthetic device having an alternative conductive adhesive aid of the disclosed invention fitted thereto.
Figure 6:
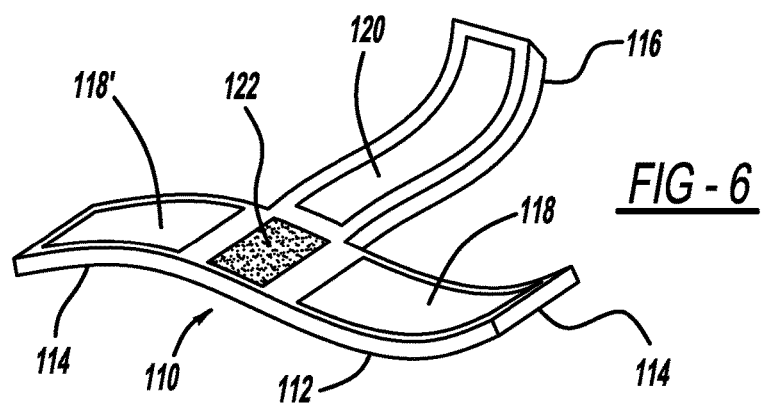
FIG. 6 is a perspective view of an embodiment of a conductive adhesive aid of the disclosed invention in the form of a conductive adhesive patch.
Figure 5:
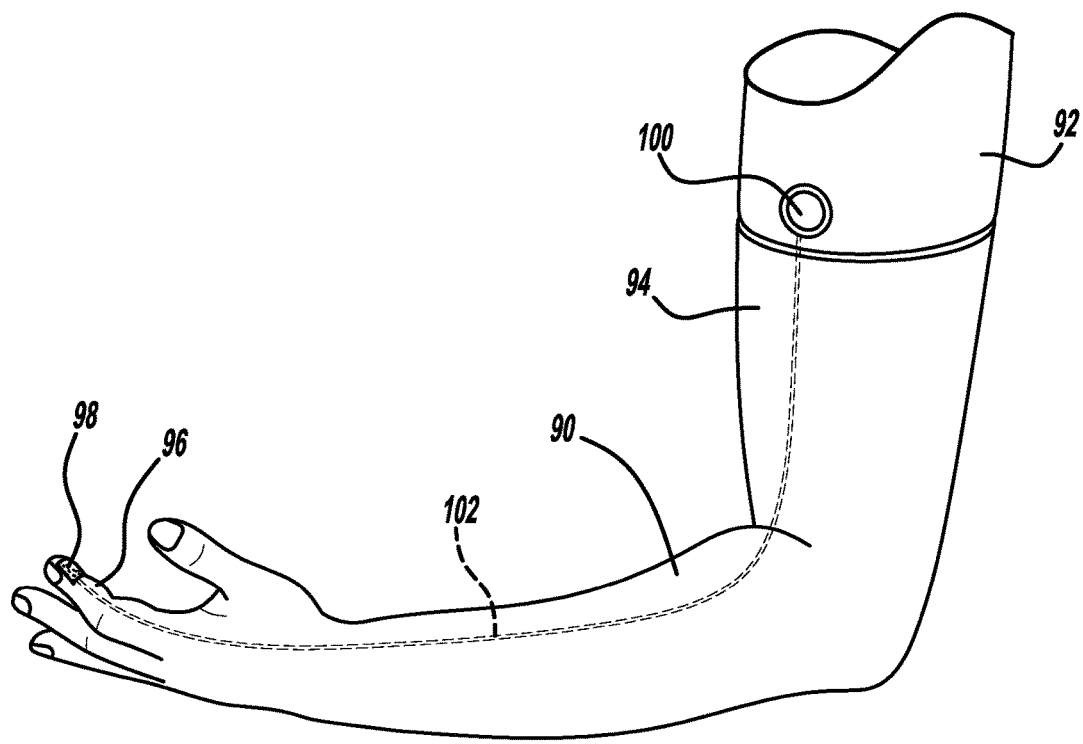
FIG. 5 is a side view of a prosthetic device having an alternative conductive adhesive aid of the disclosed invention fitted thereto.
Figure 7:
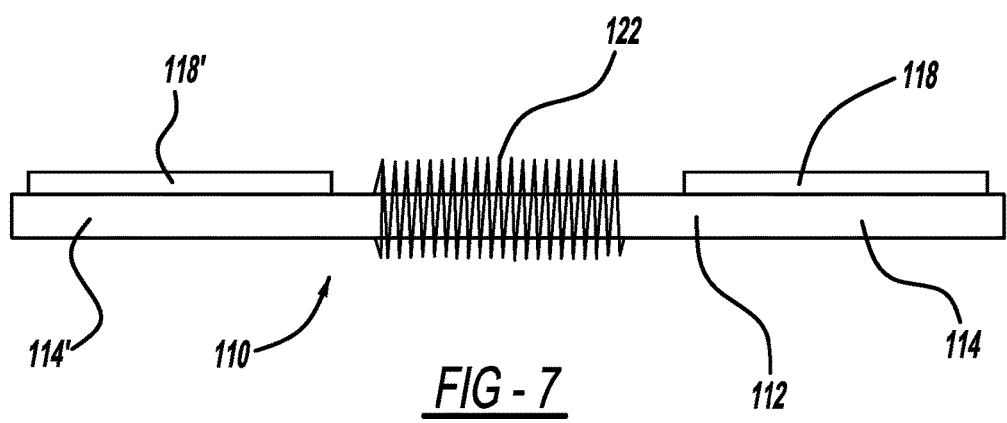
FIG. 7 illustrates a side view of the conductive adhesive patch of FIG. 6.
Figure 8:
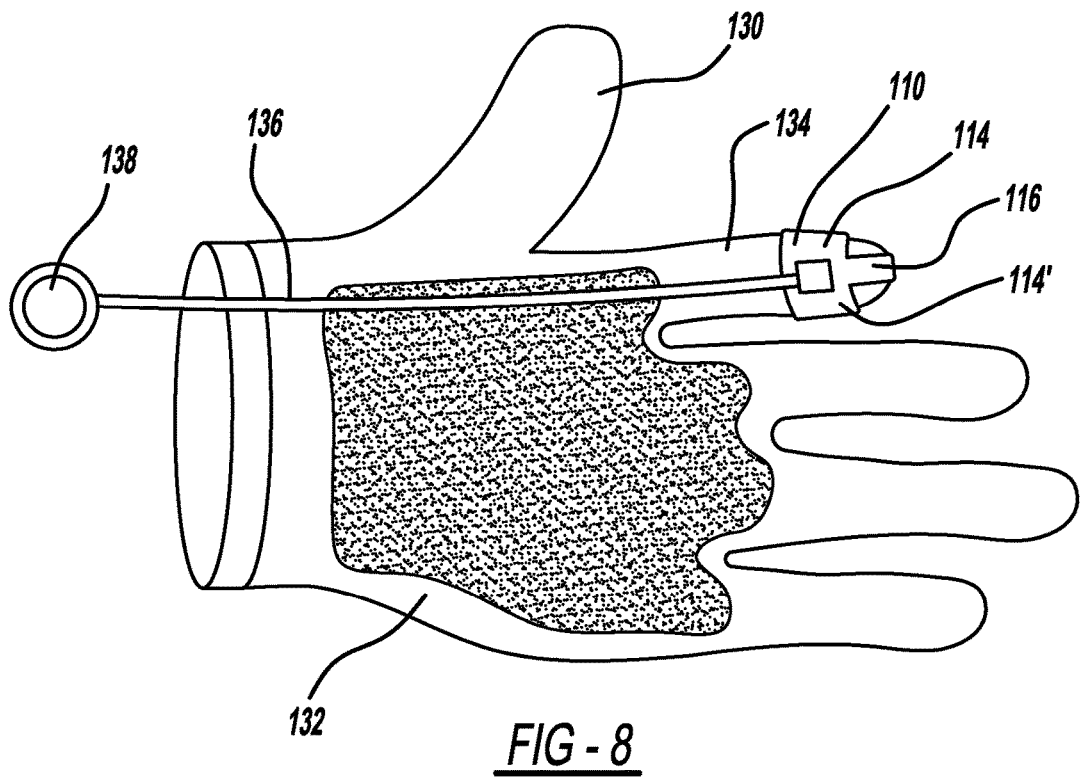
FIG. 8 illustrates a glove with the conductive adhesive patch of FIGS. 6 and 7 in position on a glove.

FIGS. 3 through 5 relate to an aid according to a first embodiment of the disclosed invention that may be attached to standard prosthetic limbs. FIGS. 6 through 8 relate to an adhesive patch that may be used directly on the skin or may be attached to a user's glove.

With reference to FIG. 3, a side view of a prosthetic device 50 is illustrated. The prosthetic device 50 is attached to the wearer's arm 52. The prosthetic device 50 includes a body portion 54 and a finger portion 56. The finger portion 56 includes a movable finger 58 and a fixed finger 60.

Attached to the tip of the fixed finger 60 is an aid of the disclosed invention in the form of a pad 62. The back side of the pad 62 includes an adhesive for attachment to the tip of the fixed finger 60.

The front side of the pad 62 includes an electrically conductive medium, such as a conductive wire or conductive foam.

An optional skin-contacting adhesive patch 64 is provided for attachment to the user's skin. The skin-contacting adhesive patch 64 includes an adhesive portion for attachment to the skin and a conductive portion that is placed into contact with the wearer's skin when the skin-contacting adhesive patch 64 is used. An optional conductive line 66 is partially embedded in the prosthetic device 50 and connects the electrically conductive medium of the pad 62 with the conductive portion of the skin-contacting adhesive patch 64.

With respect to FIG. 4, an alternate configuration of a prosthetic device is shown, illustrated as prosthetic device 70. The prosthetic device 70 is attached to the user's forearm 72.

The prosthetic device 70 includes a body portion 74 and a finger 76. Attached to the finger 76 is an aid of the disclosed invention in the form of a pad 78. The back side of the pad 78 includes an adhesive for attachment to the tip of the finger 76.

The front side of the pad 78 includes an electrically conductive medium, such as a conductive wire or conductive foam.

An optional skin-contacting adhesive patch 80 is provided for attachment to the user's skin. The skin-contacting adhesive patch 80 includes an adhesive portion for attachment to the skin and a conductive portion that is placed into contact with the wearer's skin when the skin-contacting adhesive patch 80 is used. An optional conductive line 82 is almost entirely embedded in the prosthetic device 70 and connects the electrically conductive medium of the pad 78 with the conductive portion of the skin-contacting adhesive patch 80.

With respect to FIG. 5, an additional alternate configuration of a prosthetic device is shown, illustrated as prosthetic device 90. The prosthetic device 90 is attached to the user's arm 92.

The prosthetic device 90 includes a body portion 94 and a finger 96. Attached to the finger 96 is an aid of the disclosed invention in the form of a pad 98. The back side of the pad 98 includes an adhesive for attachment to the tip of the finger 96.

The front side of the pad 98 includes an electrically conductive medium, such as a conductive wire or conductive foam.

An optional skin-contacting adhesive patch 100 is provided for attachment to the user's skin. The skin-contacting adhesive patch 100 includes an adhesive portion for attachment to the skin and a conductive portion that is placed into contact with the wearer's skin when the skin-contacting adhesive patch 100 is used. An optional conductive line 102 is almost entirely embedded in the prosthetic device 90 and connects the electrically conductive medium of the pad 98 with the conductive portion of the skin-contacting adhesive patch 100.

It is to be understood that while the embodiments of the disclosed invention of FIGS. 3, 4 and 5 illustrate the use of a skin-contacting adhesive patch 64, 80 and 100, another means of contacting the skin of the wearer may be employed, such as having an optional electrically conductive surface formed on an inner wall of the prosthetic device 50, 70 or 90 respectively such that the wearer's skin is brought into contact with the electrically conductive surface when the prosthetic device is fitted. An optional conductive line such as one of conductive lines 66, 82 or 102 would connect the electrically conductive surface with the pad 62, 78 or 98 respectively.

FIGS. 6 and 7 disclose an alternate embodiment of the aid of the disclosed invention. This embodiment may be used either as a bandage for a wounded or compromised finger.

Referring to both FIGS. 6 and 7, an adhesive bandage 110 is illustrated. The bandage 110 has a flexible body 112. As a preferred embodiment of the adhesive bandage 110 a first arm 114, a second arm 114', and a third arm 116 extend from the flexible body 112. A greater or lesser number of arms may be selected.

The back sides of the arms are provided with an adhesive for removable attachment to the user. The first arm 114 includes an adhesive 118, the second arm 114' includes an adhesive 118', and the third arm 116 includes an adhesive 120. The adhesives 118, 118' and 120 may be selected from any one of several known adhesives appropriate for the stated purpose.

A conductive surface 122 is optionally included to provide conductivity between the user's fingertip skin and the capacitive touchscreen. The conductive surface may be a conductive thread, conductive foam, or any other conductive material.

FIG. 8 illustrates an additional application of the adhesive bandage 110 of FIGS. 6 and 7. With respect to FIG. 6, the adhesive bandage 110 is illustrated in use with a glove 130. The glove 130 includes a palm side 132 and an index finger part 134.

According to this use, the adhesive bandage 110 is not in direct contact with the skin. Instead a conductive line 136 is attached at one end to the conductive surface 122 and at the other end to a skin-contacting adhesive patch 138. The skin-contacting adhesive patch 138 is provided for attachment to the user's skin in the same manner as the skin-contacting adhesive patches 64, 80 and 100 discussed above with respect to FIGS. 3, 4 and 5. The skin-contacting adhesive patch 138 includes an adhesive portion for attachment to the skin and a conductive portion that is placed into contact with the wearer's skin when the skin-contacting adhesive patch 138 is used. It is to be understood that while the embodiments of the disclosed invention of FIG. 8 illustrates the use of a skin-contacting adhesive patch 138, another means of contacting the skin of the wearer may be employed such as having an optional electrically conductive surface formed on an inner wall of the grove 130 respectively such that the wearer's skin is brought into contact with the electrically conductive surface when the glove is fitted.

Figure 9:
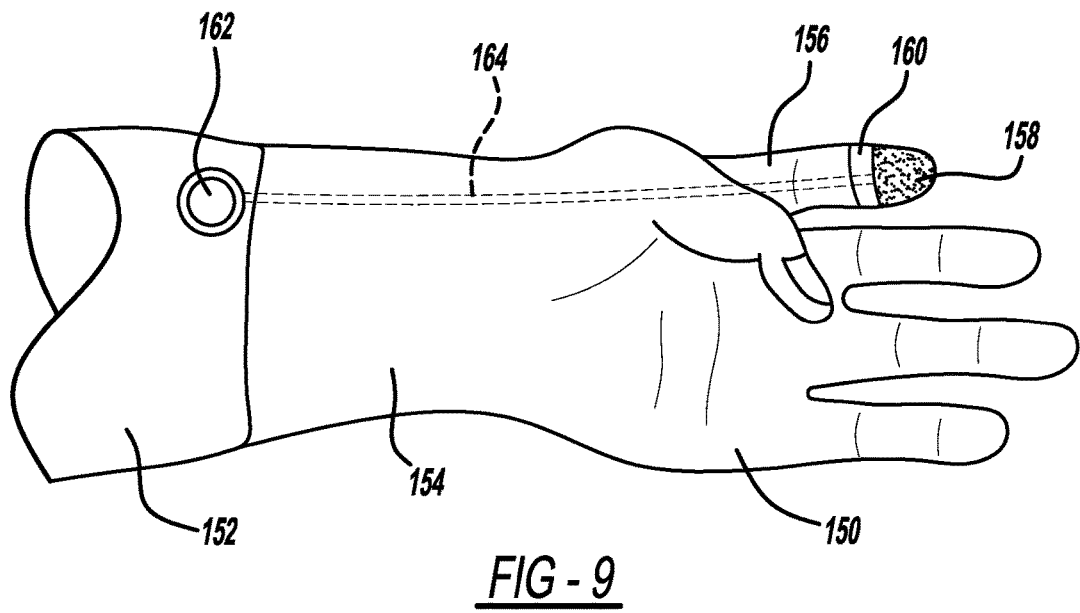
FIG. 9 is a palm side view of a prosthetic device having a factory integrated conductive tip.
Figure 10:
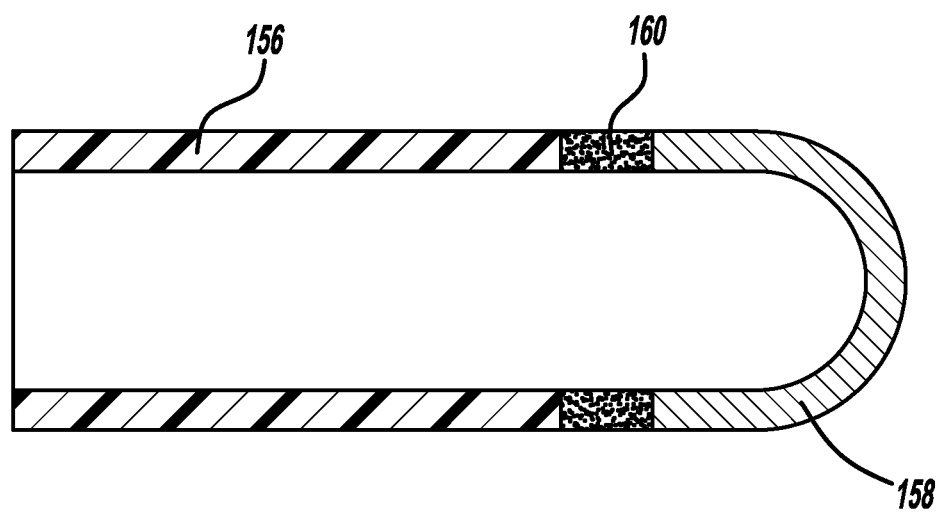
FIG. 10 is sectional view of a portion of the prosthetic device of FIG. 9 and illustrating the factory integrated conductive tip in section.

As a further alternate embodiment of the disclosed invention, a conductive element may be provided as a factory integrated conductive tip. This embodiment is shown in FIGS. 9 and 10 in which a prosthetic device 150 is shown attached to the wearer's arm 152. The prosthetic device 150 includes a body portion 154 and a finger portion 156. The finger portion 156 includes an integrated conductive tip 158. The integrated conductive tip 158 may be attached to the finger portion 156 by any of several known arrangements, such as by an attachment band 160. The integrated conductive tip 158 may be made from any of several known conductive materials discussed above in relation to other embodiments of the disclosed invention.

An optional skin-contacting adhesive patch 162 may be provided for attachment to the user's skin. The skin-contacting adhesive patch 162 includes an adhesive portion for attachment to the skin and a conductive portion that is placed into contact with the wearer's skin when the skin-contacting adhesive patch 162 is used. A conductive line 164 is partially embedded in the prosthetic device 150 and connects the electrically conductive medium of the tip 158 with the conductive portion of the skin-contacting adhesive patch 162.

Each of the embodiments of the aid of the disclosed invention set forth above overcomes the challenges faced by prosthetic device wearers and by persons needing to wear a bandage or wearing a glove. It is to be understood that the foregoing discussion discloses and describes exemplary embodiments of the disclosed invention. One skilled in the art will readily recognize from such discussion, and from the accompanying drawings and claims that various changes, modifications and variations can be made therein without departing from the true spirit and fair scope of the invention as defined by the following claims.

What is claimed is:

1. A prosthetic device comprising:
   a body portion including a limb-attachment end;
   a finger portion extending from the body portion, said finger portion including an integrated conductive tip and an attachment band, said conductive tip being attached to said finger portion by said attachment band;
   a conductive line attached at a first end to the integrated conductive tip and at least partially embedded in the body portion; and
   a second conductive portion attached to a second end of the conductive line, wherein said limb-attachment end is selected from the group consisting of:
   (a) a forearm attachment end; and
   (b) an upper arm-attachment end.

2. The prosthetic device of claim 1, wherein the second end of the conductive line includes an adhesive patch.

3. A prosthetic limb comprising:
   a prosthetic finger having a tip;
   an attachment band; and an integrated conductive tip integrated with said prosthetic finger, said conductive tip encompassing said tip of said prosthetic finger, said conductive tip being attached to said tip of said finger by said attachment band.

4. The prosthetic limb construction of claim 3 further including a conductive line connected to said conductive tip and a skin-contacting adhesive patch connected to said conductive line.

5. The prosthetic limb construction of claim 4 wherein said skin-contacting adhesive patch includes a conductive portion, said conductive line being connected to said conductive portion.

6. A prosthetic hand comprising:
   a body portion;
   a finger portion extending from the body portion;
   an attachment band;
   an integrated conductive tip integrated with the finger portion by said attachment band;
   a conductive line coupled to the conductive tip and at least partially embedded in the body portion and the finger portion; and
   an adhesive patch that is coupled to the conductive line and that includes a conductive portion.

* * * * *